United States Patent [19]

Syed

[11] Patent Number: 4,579,131

[45] Date of Patent: Apr. 1, 1986

[54] HAIR SOFTENING METHOD AND COMPOSITIONS

[76] Inventor: Ali N. Syed, 3508 Woodworth Pl., Hazel Crest, Ill. 60429

[21] Appl. No.: 748,752

[22] Filed: Jun. 26, 1985

[51] Int. Cl.$^4$ ............................................. A45D 7/00
[52] U.S. Cl. ......................................... 132/7; 424/70
[58] Field of Search ......................... 132/7; 424/70-72

[56] References Cited

U.S. PATENT DOCUMENTS

| | | | |
|---|---|---|---|
| 3,912,808 | 10/1975 | Sokol ................................... | 424/71 |
| 3,915,904 | 10/1975 | Tonkyn et al. ...................... | 528/405 |
| 3,953,330 | 4/1976 | Tonkyn et al. ...................... | 210/728 |
| 4,175,572 | 11/1979 | Hsiung et al. ...................... | 132/7 |
| 4,237,910 | 12/1980 | Khahil et al. ....................... | 132/7 |

*Primary Examiner*—Gregory E. McNeill
*Attorney, Agent, or Firm*—Esther O. Kegan; John H. Shurtleff

[57] ABSTRACT

A hair softening method and compositions for hair treatment which require the use of an essential softening agent as obtained substantially as recommended in U.S. Pat. No. 3,915,904 by the polymerization of an epihalohydrin and an alkylene polyamine of the formula

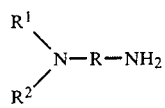

wherein R is lower alkylene of about 2 to 6 carbon atoms and $R^1$ and $R^2$ are each lower alkyl of about 1 to 6 carbon atoms, the resulting polymer being crosslinked by at least a minor proportion of the epihalohydrin used in the polymer.

8 Claims, No Drawings

HAIR SOFTENING METHOD AND COMPOSITIONS

BACKGROUND OF THE INVENTION

Many hair treatment processes, such as permanent waving or curling, bleaching, coloring or dyeing, straightening and shampooing cause a degree of damage to the hair, leaving it with a harsh feel and often making it difficult to comb or manage in subsequent hair cutting, styling or general daily care. In order to overcome these problems, it has been common to use various softening agents in the form of hair conditioners or creme rinses, usually applied to the hair in a separate step after the treatment which caused the problem. Cationic softening agents have been most popular for this purpose, especially the cationic fatty quaternary compounds having fatty chain lengths of about 8 to 18 carbon atoms. Most of the known softeners or hair conditioners do not work well when incorporated into other hair treatment compositions, including shampoos as well as waving, coloring, bleaching and straightening compositions, and it is for this reason that the hair conditioners are practical only as a special post-treatment composition.

According to Phillip E. Sokol in U.S. Pat. No. 3,919,808 and Du Y. Hsiung et al in U.S. Pat. No. 4,175,572, it has been possible to use polymers of diallyl dialkyl ammonium salts, for example a polymer of diallyldimethylammonium chloride, in order to soften the hair during such known treatments as curling, bleaching, coloring and straightening of hair. The Sokol patent is of particular interest because it describes the state of the art during the early 1970's and the lack of any real solution to the problem of providing a hair softener or conditioner which is compatible with other hair treating processes or compositions. Sokol provides only one solution to the known problems and demands the use of a relatively expensive class of polymers or copolymers, prepared according to Butler et al in U.S. Pat. No. 2,926,161, using a free radical generating polymerization catalyst such as a peroxide, and then adopting an anion exchange column to exchange the anion, if desired, according to U.S. Pat. No. 3,288,770 and U.S. Pat. No. 3,412,019.

The Sokol patent does provide useful definitions of various hair treatment compositions, and this subject matter is therefore incorporated herein by reference as fully as if set forth in its entirety, since the present invention is also directed to the same types of compositions.

It is an object of the present invention to provide an improved method of softening or conditioning hair by using a class of cationic compounds which are highly compatible with the known compositions and methods used to curl, wave, bleach, dye, color, straighten and/or shampoo the hair. It is also an object of the invention to provide such a conditioner or softener which can be used before, during or after other hair treatments, so that the hair is easier to manage and comb at any stage during its treatment or care. It is also an object of the invention to provide a cationic conditioner or softener and methods for its application whereby the conditioned hair will retain its soft feel and manageability for a relatively long period of time even after final rinsing and drying.

SUMMARY OF THE INVENTION

It has now been found in accordance with the invention that an improved method of softening hair can be achieved by the steps which comprise:

(a) applying to the air an aqueous hair treatment composition containing a softening amount of a water-soluble cationic polymer obtained by the polymerization of an epihalohydrin and an alkylene polyamine having the formula

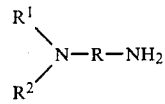

wherein R is lower alkylene of about 2 to 6 carbon atoms and $R^1$ and $R^2$ are each lower alkyl of about 1 to 6 carbon atoms, the resulting polymer being branched and crosslinked by at least a minor proportion of the epihalohydrin used in the polymer;

(b) retaining said composition in contact with the hair for a period of time sufficient to evidence a softening effect; and (c) then rinsing the hair with water to dilute and substantially remove excess material of said composition which does not combine with the hair.

The preferred alkylene polyamines are those in which R is propylene and in which $R^1$ and $R^2$ each represent methyl or ethyl. The preferred epihalohydrins are epichlorohydrin and epibromohydrin.

It was further discovered that the water-soluble cationic polymer required for the method of the invention is compatible with conventional hair treatment compositions so as to be added or combined to achieve a single formulation which will retain the desirable hair treating properties such as curling, bleaching, coloring or shampooing while also softening the hair. The resulting new formulations or compositions according to the invention can be defined as comprising a solution in water of the above-described cationic polymer as obtained by polymerization of an epihalohydrin with the alkylene polyamine and one of the following known hair treatment compositions:

(a) alkaline hair curling, hair waving or hair straightening compositions;

(b) acidic neutralizing solutions as used to rinse and neutralize an alkaline hair treatment composition;

(c) peroxide hair bleaching compositions;

(d) alkaline depilatory cream compositions; and (e) alkaline to neutral shampoo compositions.

These various novel compositions are discussed and exemplified below, but it is sufficient for purposes of defining the new formulations of the invention to simply identify the pinciple ingredient used to obtain a particular kind of hair treatment in admixture with the essential softener which is the cationic polymer of the epihalohydrin and the alkylene polyamine admixture or blendine, can occur in situ, i.e. on the hair itself. This cationic polymer as a softener appears to function almost independently of the other components of the known hair treatment compositions and to be retained with the hair whether added before, during or after application of the other hair treating agents and the associated auxiliaries or additives which complement the particular hair treating agent Thus, it is appropriate to define the new formulations as the known hair treatment composition improved by the addition of the essential cationic polymer.

DETAILED DESCRIPTION OF THE INVENTION

The process of preparing the particular cationic polymer used as the softening agent of the present invention is quite critical as will be apparent from the description in U.S. Pat. No. 3,915,904, since it is desirable there and also for purposes of the present invention to ensure at least a minimal branching and crosslinking with a certain proportion of the total moles of epihalohydrin used in the polymer.

The proportions of epihalohydrin to the alkylene polyamine are generally in a range of about 0.6:1 to 2.7:1 and preferably about 0.75:1 to 1.3:1, expressed as a molar ratio. The polymerization itself is carried out at about 60° to 120° C. and preferably about 80° to 110° C. while reacting only part of the total amount of the epihalohydrin, preferably about 50 to about 90% of the total moles to be polymerized. These proportions and reaction conditions should generally correspond to those taught in U.S. Pat. No. 3,915,904, including all preferred proportions and conditions as well as carrying out the reaction in an aqueous medium of alkaline pH, i.e. about 7.5 to 12 and preferably 8 to 11. Then, after the polymerization is completed and the final viscosity of the reaction medium is attained, it is possible according to the teaching of U.S. Pat. No. 3,915,904 to stabilize the reaction medium to a pH of from about 1 to 7 and especially about 2 to 5 by adding a mineral acid, e.g. hydrochloric, sulfuric, nitric and/or phosphoric acid, or else a strong organic acid. When used in certain alkaline hair treatment compositions of the present invention, the cationic polymer may be used directly without acid stabilization or else stabilized to an approximately neutral pH, e.g. between 6 and 8.

For purposes of the present invention, it is preferable to maintain the final polymer at a molecular weight and viscosity such that it is fully water-soluble and will not gel even in tis pure liquid form or when highly concentrated for shipment and subsequent redissolving or dilution in the desired quantity of water. The most desirable viscosities are considered to be in a range of about 10 to 2,000 centipoises, measured at a 20 percent concentration of the polymer in water. The calculated molecular weight of the preferred polymers is in a range of about 4,000 to 500,000.

It is essential for purposes of the present invention that the polymers exhibit substantial branching and crosslinking in the molecule, and the best results appear to be obtained when following the procedural steps and reaction conditions set forth in U.S. Pat. No. 3,915,904. For example, although one can first react from about 50 to 90% of the total moles of epihalohydrin to be polymerized during the first stage of the polymerization reaction and then add all of the remaining epihalohydrin at one time for the second stage of the reaction, it is preferable to add the remaining epihalohydrin incrementally during the second stage as a means of better controlling the final viscosity and the degree of crosslinking. Also, each increment is substantially fully reacted before the next increment is added, with reference to the available reaction sites on the epihalohydrin. The increments are preferably added in progressively smaller amounts to further maintain control over the properties of the final product. Such procedures avoid the formation of a polymeric gel which is not readily dispersed in water. On the other hand, a high degree of branching and crosslinking appears to enhance the hair softening properties of these polymers as long as they can still be dissolved or readily dispersed in water so that it is feasible to use somewhat higher proportions of the epihalohydrin when preparing the polymer, i.e. as total moles and in the proportion incrementally added to achieve branching and crosslinking.

The actual chemical structure of these particular cationic polymers has not been established, but one can assume the structure set forth in U.S. Pat. No. 3,915,904 as being reasonably accurate and highly descriptive of the polymer chain and its combination of tertiary amine units "x" and quaternary ammonium units "y" with linear and branched or crosslinking units derived from the epihalohydrin. Again, the disclosure of U.S. Pat. No. 3,915,904 is fully incorporated herein as to this presumed chemical structure of the polymer which can be illustrated as follows:

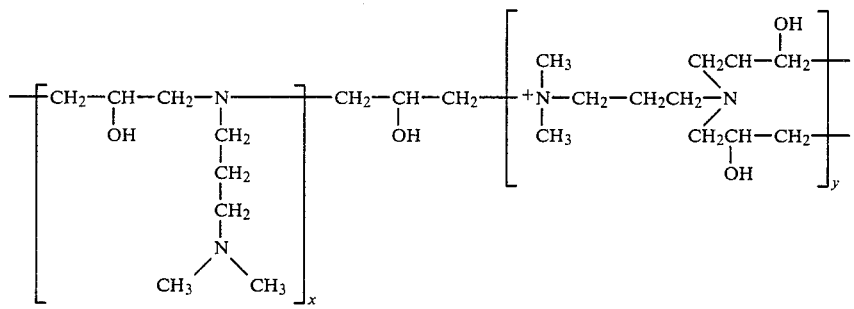

where, according to the patent, x is greater than y. In the present invention, the ratio of x:y is preferably in a range of about 1:4 to 4:1 and especially about 3:2 to 2:3.

The invention is further illustrated by the following examples using commercially available water-soluble cationic alkylene polyamines as discussed above and obtainable in their pure liquid form under the trademarks Betz ® Polymer 1177 and Betz ® Polymer 1180 from the Betz Company of Trevose, Pa. 19045. These products were developed for use as coagulants or flocculants for waste waters and have been identified as the polymerization products of epichlorohydrin with a selected N,N-dialkyl-propylene diamine, especially N,N-dimethyl propylene diamine. An analysis of the Polymer 1180 establishes the presence of both the epichlorohydrin and the tertiary dimethyl amino group as well as the primary amino group of the N,N-dimethyl propylene diamine.

The following examples also illustrate preferred hair treatment compositions according to the present invention where the combination of a softener with well known hair curling, straightening, coloring, bleaching, depilatory or shampooing compositions is highly desirable. It will be understood that these examples are intended as being illustrative only and that the invention is not limited to these examples. Parts or proportions are by weight percent of the total composition unless otherwise noted.

EXAMPLE 1

Curling Method

Polymer 1177 and Polymer 1180 were incorporated at various levels in Composition A which is an emulsion containing ammonium thioglycolate as the essential reducing agent to curl hair:

| Composition A (Curling Lotion) | Weight Percent |
| --- | --- |
| Water Deionized | 69.85 |
| Tetrasodium EDTA | 0.25 |
| Mineral Oil | 8.00 |
| Emulsifying Wax N.F. | 10.00 |
| Cetyl Alcohol | 1.00 |
| Ceteth 20 | 1.00 |
| Perfume | 0.90 |
| Ammonium Thioglycolate | 9.00 |
| Ammonium Hydroxide added to provide a pH of 9.40 | |

To one portion of Curling Lotion of Composition A, there was added 4.0% by weight of Polymer 1177 or Polymer 1180 in the form of their 20-25% by weight aqueous solutions, respectively. The hair was rolled on the desired size curling rods and one half side of the head was saturated with Curling Lotion containing the Polymer 1177 or 1180 and the other half side was saturated with Curling Lotion without the added Polymer 1177 or 1180. These solutions were left on the hair in each instance for 15-30 minutes until the desired curls were formed. At this stage, both sides of the head were rinsed with lukewarm water for two to three minutes and then an acidic Neutralizing Solution without Polymer 1177 or Polymer 1180 was applied on the rods. After 3 to 5 minutes, the hair was rinsed and the same Neutralizing Solution applied again. The hair was then rinsed again with lukewarm water and the curling rods were removed. The hair was rinsed for the last time with lukewarm water and the two half sides were compared for feel and ease of combing (wet and dry).

The half side treated with Curling Lotion containing Polymer 1177 or Polymer 1180 showed better ease of wet and dry combing and the hair felt soft. The results were very similar with both Polymer 1177 and Polymer 1180. A difference in improved softness and combability was still apparent when as little as 0.10% of the polymer or as much as 15% were used.

EXAMPLE 2

Neutralization in Curling Method

Polymers 1177 and 1180 were incorporated at various levels into Neutralizing Solutions B and C:

| Composition B (Neutralizer) | Weight Percent |
| --- | --- |
| Water Deionized | 86.87 |
| Sodium Bromate | 13.00 |
| Disodium Phosphate | 0.13 |
| Citric Acid to pH | 7.40 |

| Composition C (Neutralizer) | Weight Percent |
| --- | --- |
| Water Deionized | 94.24 |
| Phenacetin | 0.05 |
| $H_2O_2$(35%) | 5.71 |
| Phosphoric Acid to pH | 4.00 |

To one portion of the Neutralizer B or C, there was added 4.0% by weight of Polymer 1177 or Polymer 1180 in the form of a 20-25% by weight of aqueous solution, respectively. The hair was rolled on the desired size curling rods and was saturated with the Curling Solution of Example 1, but without Polymer 1177 or Polymer 1180, for 15-30 minutes. The whole head was then rinsed out with lukewarm water for 2-3 minutes and one half side of head was treated in separate tests with each of the Neutralizing Solutions B and C containing Polymer 1177 or Polymer 1180 in each case. The other side of the head was treated with the same Neutralizing Solution but without Polymer 1177 or Polymer 1180. The two different solutions were left on the hair for the same period of 3-5 minutes and then rinsed away using lukewarm water. Each half side was resaturated using the same Neutralizing Solutions as used before on each half side, again for 3-5 minutes. Then the rods were taken out of the hair. The whole head was rinsed with lukewarm water and each side was combed while wet and dry. The side which was treated with Neutralizing Solution containing Polymer 1177 or Polymer 1180 combed significantly easier in both wet and dry stages. The hair felt soft during wet and dry stages. There was no need for applying a softening cream rinse or any other convetional conditioner to the side which was treated with Polymer 1177 or Polymer 1180.

The results of an improved softening effect were quite similar whether using either of the Neutralizing Solutions B or C in combination with either of the Polymers 1177 or 1180. These improved results were still apparent when as little as 0.10% of the polymers or as much as 15.0% were used.

EXAMPLE 3

Bleaching Method

Two volumes of Composition D and one volume of Composition E below were combined along with 4.0% by weight of Polymers 1170 and 1180 of Example 1.

| Composition D | Weight Percent |
| --- | --- |
| Water Deionized | 71.45 |
| Phenacetin | 0.05 |
| Dehydag Wax O | 9.00 |
| Stearic Acid | 0.50 |
| Hydrogen Peroxide (35%) | 17.00 |
| Peg-20 Stearate | 2.00 |

| Composition E | Weight Percent |
| --- | --- |
| Water Deionized | 75.00 |
| Emulsifying Wax N.F. | 3.00 |
| Cetyl Alcohol | 8.00 |
| Petrolatum IS | 7.0 |
| NH₄OH 28° | 7.0 |

In each test, a mixture of Composition D and E and one of the polymers of Example 1, was applied to hair and allowed to stand on the hair for 10–80 minutes depending upon the extent of bleaching required. The hair was then rinsed and shampooed with a standard non-detangling shampoo. The hair treated in this way according to the invention exhibited ease of wet combing and softer feel as compared to hair which was treated with the same bleaching composition not containing Polymer 1177 or Polymer 1180.

EXAMPLE 4

Straightening Method

Polymer 1177 and Polymer 1180 were incorporated into the following Hair Straightening composition F:

| Composition F | Weight Percent |
| --- | --- |
| Protopet IS | 15.00 |
| Carnation Oil | 25.00 |
| Stearyl Alcohol | 12.00 |
| Laureth-12 | 2.00 |
| Tegacid Special | 2.00 |
| Water Deionized | 42.00 |
| Sodium Hydroxide | 2.00 |

To one portion of Hair Straightening Composition F, there was added 4.0% by weight of Polymer 1177 or Polymer 1180 in the form of a 20–25% by weight aqueous solution, stirring or mixing with a wooden spatula to achieve a uniform mixture. This resulting mixture was applied to one half side of the head and the other half side of the head was treated with the same Hair Straightening composition F but without the added Polymer 1177 or 1180. Both sides were washed twice with an acidic non-detangling Shampoo H as described below. The hair was combed and the half side of the head treated with the polymer-containing Hair Straightener was significantly easier to comb in wet and dry stage and also very manageable when dry. The results with each of the Polymers 1177 and 1180 were very similar. This improvement was still apparent when as little as 0.25% of the polymers or as much as 15.0% were used.

EXAMPLE 5

Straightening Method

Another Hair Straightener G was also applied to the hair where the straightening agent was ammonium bisulfite. This experiment was conducted the same way as in Example 4 and the results were very similar to Example 4.

| Composition G | Weight Percent |
| --- | --- |
| Water Deionized | 69.50 |
| Isopropanol | 5.00 |

| Composition G | Weight Percent |
| --- | --- |
| Dimethyl Urea | 15.00 |
| Hydroxyethyl Cellulose | 1.50 |
| Ammonium Bisulphite | 9.00 |
| Aqua Ammonia (26°) added to provide a pH of 7.0 | |

EXAMPLE 6

Shampoo Method

A Shampoo composition H was prepared as follows:

| Composition H | Weight Percent |
| --- | --- |
| Water Deionized | 68.40 |
| Methylparaben | 0.10 |
| Propylparaben | 0.10 |
| Imidazolidinyl Urea | 0.20 |
| Disodium EDTA | 0.20 |
| Miranol C2M SF Conc. (40%) | 20.00 |
| Ammonium Lauryl Sulfate | 3.00 |
| Cocoamide DEA | 4.00 |
| Polysorbate-80 | 3.00 |
| Glucomate DOE 120 | 1.00 |
| Citric Acid added to provide a pH of 6.0 | |

To one portion of the shampoo was added 4.0% by weight of the Polymer 1177 used in Example 1. The samples of the shampoo with and without the added polymer were then employed to treat each designated half side of the head under the same conditions. The hair was washed twice with these shampoos and rinsed with lukewarm water at the end. The hair washed with shampoo containing Polymer 1177 was soft, lustrous and easy to comb both wet and dry in contrast to the other shampoo which was harsh, difficult to comb and readily tangled. The above experiment was repeated with Polymer 1180 and the results were similar. The improvement in each case was still apparent when as little as 0.25% of the polymer or as much as 15.0% were used.

EXAMPLE 7

Depilatory Method

Polymer 1177 and Polymer 1180 were incorporated at various levels in a Depilatory Cream J:

| Composition J | Weight Percent |
| --- | --- |
| Water Deionized | 71.50 |
| Tetrasodium EDTA | 0.20 |
| Emulsifying Wax N.F. | 10.00 |
| Cetyl Alcohol | 3.00 |
| Sodium Silicate O | 3.00 |
| Thioglycolic Acid | 4.00 |
| Sodium Hydroxide | 2.30 |
| Calcium Hydroxide | 6.00 |

To one portion of this Depilatory Cream J, there was added 4.0% by weight of Polymer 1177 or Polymer 1180 in the form of a 20–25% by weight aqueous solution. One half side of a facial beard was treated with Depilatory Cream J containing Polymer 1177 and the other half side was treated with Depilatory Cream J without Polymer 1177. These creams were left on the face for 8-10 minutes and then removed using a wooden spatula. The face was cleaned with a wet towel and then washed. The side treated with Depilatory Cream J containing Polymer 1177 felt soft and smooth when touched with the hand and fingers. This experiment was repeated with Depilatory Cream J containing Polymer 1180 in place of Polymer 1177 and the results were very similar. The improvement was still apparent when as little as 0.10% of the polymer or as much as 15.0% were used.

EXAMPLE 8

Additional Straightening Tests

From 0.25 to 15 grams of Polymer 1177 or Polymer 1180 as a 20-25% aqueous solution were applied directly to one half side of the head before applying Hair Straightener F described above, the polymer being combed through hair using a shampoo comb. The Hair Straightener F was then applied to both half sides of the head, keeping each side separate, and kept on each side for a specific length of time in each test, ranging between 5 and 20 minutes. The hair was then rinsed with lukewarm water and each side of the head washed with the acidic non-detangling Shampoo H. The hair was combed and the half side of the head treated with polymer was significantly easier to comb both in the wet and dry stages. The hair was very soft to feel in both stages and also very manageable when dry. This improvement was still apparent when as little as 0.25% of the polymers or as much as 15.0% were used with reference to the weight of the Straightener H.

Another Hair Straightener G as described above was also applied to the hair instead of Hair Straightener F, using the same procedure. The results were very similar in terms of softness, ease of combing and manageability when dry.

EXAMPLE 9

Straightening Cream Method

A Hair Straightener K in the form of a cream composition described below was applied to hair where the straightening agent was a mixture of guanidine carbonate solution and a calcium hydroxide cream. This experiment was conducted the same way as in Example 5 and the results were very similar to Example 5 in terms of an improvement in softness, ease of combing and manageability when dry.

The Hair Straightening Cream K is obtained by intimately mixing 212 grams of Cream (1) and 60 grams of the Liquid Activator (2). The resulting mixture can be easily applied directly to the hair and will remain in place as long as necessary to obtain a straightening effect.

| (1) Cream Composition | Weight Percent |
|---|---|
| Water Deionized | 52.50 |
| Propylene Glycol | 2.00 |
| Calcium Hydroxide | 5.00 |
| PEG-75 Lanolin | 1.00 |
| Petrolatum | 10.00 |
| Mineral Oil (Carnation Oil) | 20.00 |
| Cetereath 20 | 1.50 |
| Stearyl Alcohol | 8.00 |

| (2) Liquid Activator | Weight Percent |
|---|---|
| Water Deionized | 75.00 |
| Guanidine Carbonate | 25.00 |

EXAMPLE 10

Hair Straightening Tests in a Salon

The Hair Straightener F of Example 5 was used immediately following a preapplication of Polymer 1177 or Polymer 1180 onto half the head of 25 different subjects in a beauty salon, e.g. under natural commercial conditions but carefully controlled identical conditions for each half of the head. The control half of the head used the Straightener F without pretreatment by either polymer. The following Table I lists the properties observed by the 25 subjects in terms of a difference or clearly noticed improvement:

TABLE I

| Properties | Straightener F alone | Polymer 1177 or Polymer 1180 followed by Straightener F | No Difference Observed |
|---|---|---|---|
| 1. Consistency of the product before applying | — | — | 25 |
| 2. Consistency of the product during application | — | — | 25 |
| 3. Relaxation time 13-18 minutes | — | — | 25 |
| 4. Sensation (minor to mild) | 4 | 3 | 18 |
| 5. Relaxation (better) | 2 | 2 | 21 |
| 6. Rinsability | — | — | 25 |
| 7. Wet combing easier after shampooing with Shampoo H | — | 25 | — |
| 8. Dry combing (easier) | — | 20 | 5 |
| 9. Manageability | — | 21 | 4 |
| 10. Overall Preference | — | 23 | 2 |

In another salon test, the Hair Straightener K was used immediately following a preapplication of Polymer 1177 or Polymer 1180 onto half the head of 25 different subjects. The results are given by the following Table II:

TABLE II

| Properties | Straightener K alone | Polymer 1177 or Polymer 1180 followed by Straightener K | No Difference Observed |
|---|---|---|---|
| 1. Consistency of the product before applying | — | — | 25 |
| 2. Consistency of the product during application | — | — | 25 |
| 3. Relaxation time 13-18 minutes | — | — | 25 |
| 4. Sensation (minor to mild) | — | — | 25 |
| 5. Relaxation (better) | — | — | 25 |
| 6. Rinsability | — | — | 25 |
| 7. Wet combing easier after shampooing with Shampoo H | — | 25 | — |
| 8. Dry combing (easier) | — | 19 | 6 |
| 9. Manageability | — | 20 | 5 |

TABLE II-continued

| Properties | Straightener K alone | Polymer 1177 or Polymer 1180 followed by Straightener K | No Difference Observed |
|---|---|---|---|
| 10. Overall Preference | — | 25 | — |

The invention is hereby claimed as follows:

1. A method of softening hair which comprises:

applying to said hair an aqueous hair treatment composition containing a softening amount of a water-soluble cationic polymer obtained by the polymerization of an epihalohydrin and an alkylene polyamine having the formula

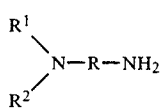

wherein R is lower alkylene of about 2 to 6 carbon atoms and $R^1$ and $R^2$ are each lower alkyl of about 1 to 6 carbon atoms, the resulting polymer being crosslinked by at least a minor proportion of the epihalohydrin used in the polymer;

retaining said composition in contact with the hair for a period of time sufficient to evidence a softening effect; and then rinsing the hair with water to dilute and substantially remove excess material of said composition which does not combine with the hair.

2. A method as claimed in claim 1 wherein R is propylene and $R^1$ and $R^2$ are each selected from the group consisting of methyl and ethyl.

3. A method as claimed in claim 1 wherein the epihalohydrin is selected from the group consisting of epichlorohydrin and epibromohydrin.

4. A method as claimed in claim 2 wherein $R^1$ and $R^2$ are each methyl and the epihalohydrin is epichlorohydrin.

5. In an aqueous hair treatment composition containing an essential hair treating component selected from the group consisting of a hair curling agent, a hair waving agent, a hair straightening agent, a hair bleaching agent, a hair coloring or dyeing agent, a hair depilatory agent and a hair shampoo agent, the improvement comprising the admixture of said hair treating component and a softening amount of a water-soluble cationic polymer obtained by the polymerization of an epihalohydrin and an alkylene polyamine having the formula

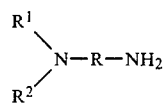

wherein R is lower alkylene of about 2 to 6 carbon atoms and $R^1$ and $R^2$ are each lower alkyl of about 1 to 6 carbon atoms, the resulting polymer being crosslinked by at least a minor proportion of the epihalohydrin used in the polymer.

6. A composition as claimed in claim 5 wherein R is propylene and $R^1$ and $R^2$ are each selected from the group consisting of methyl and ethyl.

7. A composition as claimed in claim 5 wherein the epihalohydrin is selected from the group consisting of epichlorohydrin and epibromohydrin.

8. A composition as claimed in claim 6 wherein $R^1$ and $R^2$ are each methyl and the epihalohydrin is epichlorohydrin.

* * * * *